United States Patent [19]
Nardella

[11] Patent Number: 5,713,896
[45] Date of Patent: Feb. 3, 1998

[54] IMPEDANCE FEEDBACK ELECTROSURGICAL SYSTEM

[75] Inventor: Paul C. Nardella, North Easton, Mass.

[73] Assignee: Medical Scientific, Inc., Taunton, Mass.

[21] Appl. No.: 437,962

[22] Filed: May 10, 1995

Related U.S. Application Data

[63] Continuation of Ser. No. 55,827, Apr. 30, 1993, abandoned, which is a continuation-in-part of Ser. No. 786,574, Nov. 1, 1991, Pat. No. 5,207,691, and a continuation-in-part of Ser. No. 19,334, Feb. 18, 1993, abandoned, which is a continuation of Ser. No. 786,572, Nov. 1, 1991, abandoned.

[51] Int. Cl.$^6$ .................................................. A61B 17/39
[52] U.S. Cl. ........................... 606/50; 606/42; 606/51; 606/41
[58] Field of Search ........................ 606/32, 35, 37–42, 606/45–52

[56] References Cited

U.S. PATENT DOCUMENTS

| | | | |
|---|---|---|---|
| 3,601,126 | 8/1971 | Estes | 606/35 |
| 3,913,583 | 10/1975 | Bross . | |
| 3,964,487 | 6/1976 | Judson . | |
| 4,051,855 | 10/1977 | Schneiderman | 606/51 |
| 4,092,986 | 6/1978 | Schneiderman . | |
| 4,126,137 | 11/1978 | Archibald . | |
| 4,271,837 | 6/1981 | Schuler . | |
| 4,281,373 | 7/1981 | Mabille . | |
| 4,416,276 | 11/1983 | Newton et al. . | |
| 4,474,179 | 10/1984 | Koch | 606/50 |
| 4,535,733 | 8/1985 | Yoon . | |
| 4,559,943 | 12/1985 | Bowers . | |
| 4,651,280 | 3/1987 | Chang et al. . | |
| 4,655,216 | 4/1987 | Tischer | 606/51 |
| 4,658,819 | 4/1987 | Harris et al. | 606/50 |
| 4,716,897 | 1/1988 | Noguchi et al. . | |
| 4,805,621 | 2/1989 | Heinze et al. . | |
| 4,862,889 | 9/1989 | Feucht . | |
| 4,907,589 | 3/1990 | Cosman . | |
| 4,934,377 | 6/1990 | Bova et al. . | |
| 4,961,047 | 10/1990 | Carder . | |
| 4,969,885 | 11/1990 | Farin | 606/38 |
| 5,108,391 | 4/1992 | Flachenecker et al. . | |
| 5,122,137 | 6/1992 | Lennox | 606/40 |
| 5,167,658 | 12/1992 | Ensslin . | |
| 5,167,660 | 12/1992 | Algendorf . | |
| 5,190,517 | 3/1993 | Zieve et al. . | |
| 5,269,780 | 12/1993 | Roos | 606/51 |

FOREIGN PATENT DOCUMENTS

| | | |
|---|---|---|
| 0640317 | 3/1995 | European Pat. Off. . |
| 2213381 | 8/1989 | United Kingdom . |
| WO92/14514 | 9/1992 | WIPO . |
| WO92/21300 | 12/1992 | WIPO . |
| 9320747 | 10/1993 | WIPO . |

OTHER PUBLICATIONS

Nardella, Paul, "RF Energy and Impedance Feedback" SPIE vol 1068, *Catheter Based . . . Technology,* pp. 42–48, 1989.

Nardela, Paul C., "Radio Frequency Energy and Impedance Feedback", SPIE vol. 1068, *Catheter-Based Sensing and Imaging Technology,* pp. 42–48 (1989).

*Primary Examiner*—Michael Peffley
*Attorney, Agent, or Firm*—Nutter, McClennen & Fish, LLP

[57] ABSTRACT

An impedance feedback electrosurgical system is useful with electrosurgical tools to maintain a substantially constant level of current within the tissue in contact with the tool. The system comprises active and return electrodes associated with an electrosurgical tool, an impedance monitoring device and a power control unit. Energy sufficient to affect tissue is delivered through the active electrode to tissue and to the return electrode. The impedance measuring device is in circuit with the return electrodes and measures the impedance of tissue. A signal representative of tissue impedance is communicated from the impedance measuring device to the power control unit. The power control unit adjusts the energy applied to tissue to maintain tissue impedance within a preselected and desired range.

11 Claims, 9 Drawing Sheets

IMPEDANCE FEEDBACK ELECTROSURGICAL SYSTEM

REFERENCE TO RELATED APPLICATIONS

This application is a continuation of application Ser. No. 08/055,827 on Apr. 30, 1993 (now abandoned). The contents of all of the aforementioned applications are expressly incorporated by reference, which is a continuation-in-part of U.S. patent application Ser. No. 07/786,574 filed on Nov. 1, 1991 (now U.S. Pat. No. 5,207,691), and of U.S. patent application Ser. No. 08/019,334 filed on Feb. 18, 1993 (now abandoned) which is a continuation of Ser. No. 07/786,572 filed on Nov. 1, 1991 (now abandoned).

BACKGROUND OF THE INVENTION

The present invention relates to electrosurgical tools which are adapted to deliver electrosurgical energy to tissue.

Surgical procedures often require incisions to be made in human tissue. Such procedures typically require the application of force to a surgical tool having one or more sharp, tissue-contacting edges, and usually create bleeding at the site of the incision. The ease with which the tool makes the incision and the prompt control or elimination of the bleeding thereby created is of paramount importance to the success and safety of the procedure.

Currently known surgical cutting devices utilize different techniques to make incisions and to control or eliminate bleeding. One known device is the Proximate Linear Cutter available from the Ethicon, Inc. of Cincinnati, Ohio. This device is specifically adapted to make an incision in tissue or an organ such as the intestine. The device engages a portion of the tissue or organ between two tyne-like members. To effect cutting, a blade mounted on one of the tynes travels along a predetermined path, thereby making a linear incision through the tissue or organ. Surgical staples are deployed by the cutting device on either side of the incision, resulting in the separation of the organ into two segments, each of which is sealed adjacent to the incision by surgical staples. Despite the use of surgical staples and the precise cutting of the tissue, bleeding is not entirely eliminated and separate cauterization procedures must often be utilized to control or stop bleeding.

Surgical devices also are known which utilize electrical current in the form of radio frequency (RF) energy to incise and to cauterize tissue to control bleeding. U.S. Pat. No. 4,651,734 discloses a surgical scalpel modified to include an electrode. This scalpel has the ability to cut tissue and, when properly positioned, to cauterize tissue following a cutting procedure. Such a surgical tool is useful but does not simultaneously cut and cauterize tissue. The separate cauterization procedure which must be utilized is relatively time consuming and may result in unnecessary bleeding. Moreover, such a scalpel is not well suited to many surgical procedures such as the transection of the intestine.

Typically, the surgical tools which employ RF energy to cut and cauterize do so with a constant energy supply. Because of this, the tool must be carefully controlled during surgery to ensure that the correct amount of RF energy is applied to the target tissue. For example, if a surgical tool delivers RF energy through a cutting edge to tissue at a magnitude sufficient to cut or cauterize tissue, tissue burns could result if the cutting edge contacts the tissue for too long a period. Similarly, if the cutting edge is moved too quickly through tissue, the optimal amount of energy may not be applied to the tissue. Thus, if not used properly, currently known electrosurgical tools may not take full advantage of the benefits of electrosurgery.

Accordingly, an object of this invention is to provide an electrosurgical system which enables electrosurgical tools to conveniently and safely incise and/or penetrate human tissue with controlled and precise application of RF energy. It is another object of the invention to provide a surgical tool which has improved cutting capability and which decreases some of the risk associated with surgery by minimizing the mount of bleeding resulting from incisions and tissue penetration. Another object is to provide a surgical tool which is adapted to simultaneously cut and cauterize tissue. Other objects of the invention will be apparent upon reading the disclosure which follows.

SUMMARY OF THE INVENTION

The invention attains the aforementioned objects by providing a system which measures tissue impedance as a feedback parameter from surgical tools that apply electrosurgical energy to tissue during surgery. The system is useful with a variety of electrosurgical devices including cutting tools and surgical clip applying devices.

In one aspect, an impedance feedback electrosurgical system constructed in accordance with the invention includes an electrosurgical tool which is adapted to receive power from an electrosurgical power source and to deliver electrosurgical energy to tissue through an active electrode in contact with the tissue. A return or second electrode is also associated with the tool and is electrically insulated from the active electrode. Electrosurgical energy is thus communicated from the active electrode, through the tissue, and to the return electrode.

Preferably, an impedance monitoring device is in circuit with the active and return electrodes to measure the impedance of the target tissue, which can be ascertained based upon the voltage and current of the applied energy. A power control module is also in circuit with the impedance monitoring device to regulate the electrosurgical energy delivered to the tissue through the active electrode by responding to a signal representative of tissue impedance generated by the impedance monitor. The system is able to control the electrosurgical energy applied to the tissue by maintaining a measured tissue impedance within a preselected range. The desired tissue impedance range is preferably between about 20 to 500 Ohms.

In other aspects, the impedance feedback electrosurgical system has control circuitry to enable one to select the range at which the measured tissue impedance is maintained during surgery. One or more acoustical warning devices are preferably connected in circuit with the system to warn a user that measured impedance is outside the range and to inform the user of the measured impedance.

In yet another aspect, the impedance feedback electrosurgical system regulates the energy delivered to the tissue by varying the applied voltage of the electrosurgical power source.

In still another aspect, the impedance feedback electrosurgical system controls the electrosurgical energy delivered through the delivery electrode to the tissue by an activation system. An operator can inhibit or transmit the electrosurgical energy delivered to the tissue by selectively operating the activation system, which operates much like an electrical switch.

The advantages of the electrosurgical system of the invention are several. First and foremost, by maintaining a preselected range of tissue impedance, electrosurgical energy is applied to the target tissue at a preselected level independent of the speed and operation of the tool as used by an operator or surgeon. Furthermore, when an electrosurgical tool is adapted to a system constructed in accordance with the invention, the system will inherently monitor the tool's passage through different tissue types and certain tissue barriers. For example, once the tool penetrates the abdominal wall, the current density at the active electrode will increase at the areas in contact with the electrode, and thus the applied electrosurgical energy will be automatically lowered to thereby protect that tissue from receiving excessive or unwanted RF energy.

The electrosurgical energy applied to an active electrode in accordance with the invention also improves the mechanical cutting ability of the tool, and more importantly, facilitates the cauterization and/or fusion of the tissue following the incision. The application of radio frequency energy, for example, to the tissue allows the simultaneous cutting and cauterization of the tissue with an effective consistency independent of a user's technique. Moreover, the use of electrosurgical energy to penetrate tissue can eliminate the need for a conventional, sharpened cutting blade. A conductive electrode can deliver sufficient levels of electrosurgical energy to tissue to effectively incise tissue. The electrosurgical energy also enhances other electrosurgical tools such as clip applying devices.

A method for controlling the level of electrosurgical energy applied to tissue by an electrosurgical tool is also provided by the present invention. These and other aspects of the invention are evident in the description which follows and in the accompanying drawings.

DETAILED DESCRIPTION OF THE INVENTION

Figure 1:
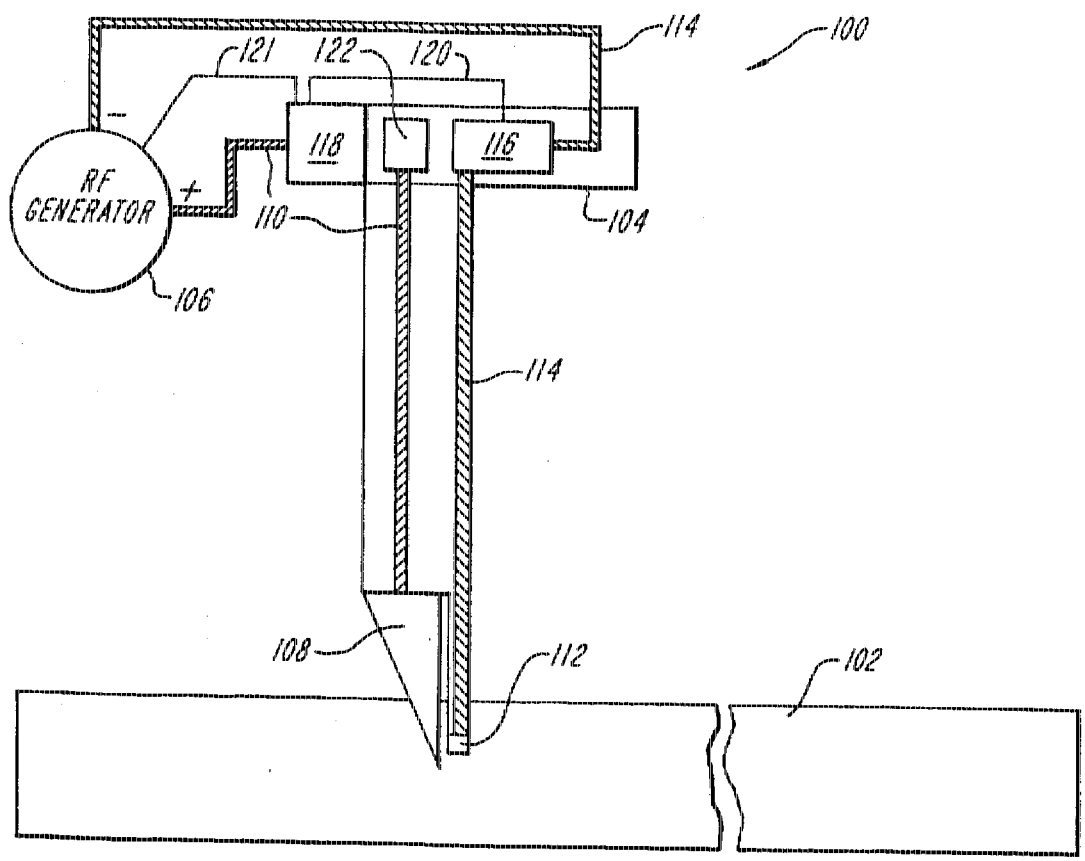
FIG. 1 schematically illustrates an impedance feedback electrosurgical system constructed in accordance with the invention and in use with an energy supply source and an electrosurgical tool.

FIG. 1 illustrates an impedance feedback electrosurgical system 100 constructed according to the present invention and in use with an electrosurgical tool 104. The system 100 includes an electrosurgical tool 104 which is connected in circuit to a power source, shown preferably as an RF generator 106. The tool 104 has an active electrode 108 which operates as a cutting edge and delivers electrosurgical energy to tissue 102. The active electrode 108 is connected to the positive pole of the electrosurgical energy supply, illustrated as an RF generator 106, through a power supply line 110. A return electrode 112 is also associated with the tool 104 and is connected to the negative pole of the electrosurgical supply 106 via a feedback line 114. An impedance monitor 116—preferably having a programmable CPU—connects in circuit with the electrodes 108 and 112 to measure tissue impedance and to generate a signal representative of tissue impedance which is conveyed to a power control module 118 through a signal line 120. The power control module 118 regulates the electrosurgical energy generated from the RF generator 106 through a control line 121 such that the impedance measured by the impedance monitor 116 remains within a preselected range. Moreover, the system preferably includes an activation switch 122 which a user can selectively operate to control the flow of energy to the delivery electrode 108.

In operation, force can be applied to the tool 104 when the active electrode 108 contacts the tissue 102 to make an incision. Electrosurgical energy applied through tool 104 heats the cells in contact with the electrodes to provide a clean incision. In the course of cutting, the electrosurgical energy applied through the tool 104 also cauterizes tissue to minimize or eliminate any associated bleeding. Without the delivery of electrosurgical energy, e.g., RF energy, through active electrode 108, the surgical incision would be less effective as it would rely solely on the mechanical sharpness of the cutting blade.

As noted, tissue impedance is maintained within a preselected range. Upon delivery of electrosurgical energy to tissue 102 through the active electrode 108, a measurable current is conveyed through the return electrode 112 for use by impedance monitor 116, where tissue impedance is determined. Accordingly, as more tissue comes into contact with the active electrode 108, the current at the return electrode 112 decreases. The impedance monitor measures this as an increase in tissue resistance (i.e., impedance) and conveys a signal representative of the measured impedance to the control module 118, which in turn makes any necessary increase in the voltage conveyed to the active electrode to maintain tissue impedance within a desired range. Where the impedance monitor 116 detects a decrease in tissue impedance below the desired minimum, the power control module 118 decreases the applied electrosurgical energy to maintain tissue impedance in the desired range. Preferably, this electrosurgical energy is in the radio frequency range, and the tissue impedance ranges between about 20 and 500 Ohms.

Figure 2:
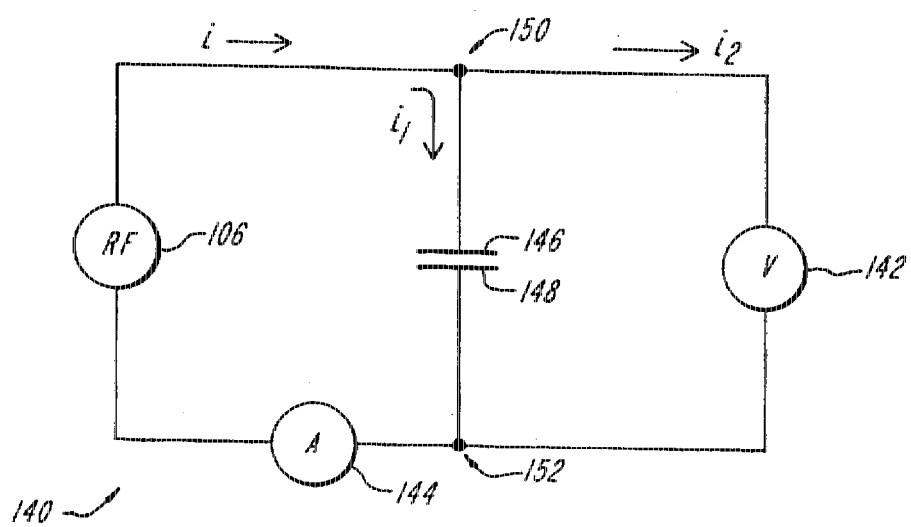
FIG. 2 schematically illustrates an electrical circuit which can be used to measure tissue impedance.

Impedance can be determined using a circuit 140 such as that shown in FIG. 2, which is illustrative and can be altered in any number of ways to function equivalently. Circuit 140 includes an RF generator 106 in circuit with a voltage sensor 142, a current sensor 144, and electrodes 146 and 148. The voltage sensor 142 measures the voltage differential between locations 150 and 152, and the current sensor 144 measures the current between the same points. The electrodes 146 and 148 can represent, respectively, the active electrode 108 and return electrode 112 of FIG. 1. Also shown in FIG. 2 are three representative currents, i, $i_1$, and $i_2$, where the current i is the current at a location immediately after the generator 106, and the currents $i_1$ and $i_2$ are currents at the respective localities after the split at location 150.

The resistance associated with the voltage sensor 142 is relatively high as compared to the rest of the circuit 140 and thus the current i is approximately equal to the current $i_1$, which can be measured. On the other hand, the resistance associated with the current sensor 144 is relatively low as compared to the rest of the circuit 140 and thus the voltage difference between locations 150 and 152 is essentially unaffected by the current sensor 144.

In circuit 140, therefore, the voltage differential between localities 150 and 152 is the same as the voltage across the electrodes 146 and 148. Since the current i is known by measuring the current $i_1$, a resistance between the electrodes 146 and 148 is also known. This resistance would be representative of the tissue impedance as described in FIG. 1. The impedance monitor 116 of FIG. 1 (not shown in FIG. 2) preferably is in circuit with the sensors 142 and 144 to divide the measured voltage by the measured current and to determine tissue impedance. A tissue impedance signal is then generated and transmitted to the power control module of FIG. 1 (not shown in FIG. 2) to regulate the applied electrosurgical energy, thereby changing the voltage measured at the voltage sensor 142 and the current measured by the current sensor 144. In this fashion, the measured tissue impedance can be monitored and controlled to within a preselected range.

The measurement of tissue impedance, e.g., corresponding to the resistance measurable in the circuit 140 of FIG. 2, is readily understood by one of ordinary skill in the art. When the current through the tissue decreases for a given applied voltage, the tissue impedance increases and is readily measured by the impedance monitor 116. Tissue cells are most effectively heated and cauterized by RF energy when the impedance is kept to within a preferred electrosurgical range, e.g., 20 to 500 Ohms. By increasing or decreasing the amount of electrosurgical energy applied to the tissue through the active electrode, tissue impedance is maintained within this range and the active electrode incises and cauterizes tissue most effectively with less chance of burning tissue. The tissue impedance is a factor of the surface area of the electrodes and distance between electrodes as well as the conductivity of the tissue and the changes created by the heating.

Additionally, the invention is able to maintain a desired tissue impedance independent of the speed with which an electrosurgical tool is used during surgery because impedance feedback is monitored and controlled automatically. Regardless of the speed at which the tool is manipulated, the effective application and beneficial usage of the electrosurgical energy remains substantially the same. If the tool is manipulated at a faster speed, the tissue impedance will measurably decrease and more energy will automatically be applied to tissue through the delivery electrode.

FIGS. 3 through 7 illustrate an embodiment of the invention in which an electrosurgical cutting tool 10 is used with the impedance feedback system of the invention. Cutting tool 10 is a linear cutting tool comprising a housing 12 including a handle portion 14. Adjacent handle portion 14 is cutting template element 16 which includes a first tyne 18 and a second tyne 20. The two tynes 18, 20 of cutting template element 16 are substantially parallel and define a tissue engaging space 22 into which is inserted the tissue or organ to be incised. In a preferred embodiment, the surgical tool 10 includes a lever 24 which facilitates the movement of an active electrode, which may take the form of a cutting blade 34, along a predetermined path.

Figure 3:
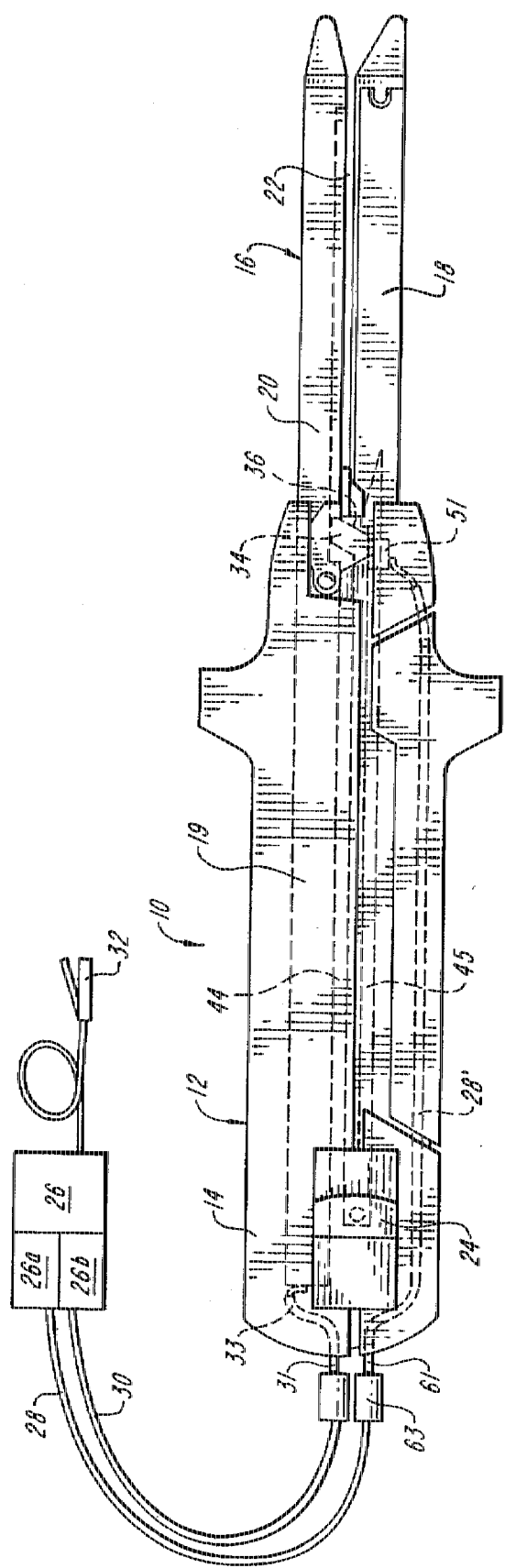
FIG. 3 schematically illustrates a surgical cutting tool employed in an impedance feedback electrosurgical system according to the invention, including a supply source of electrosurgical energy.
Figure 4:
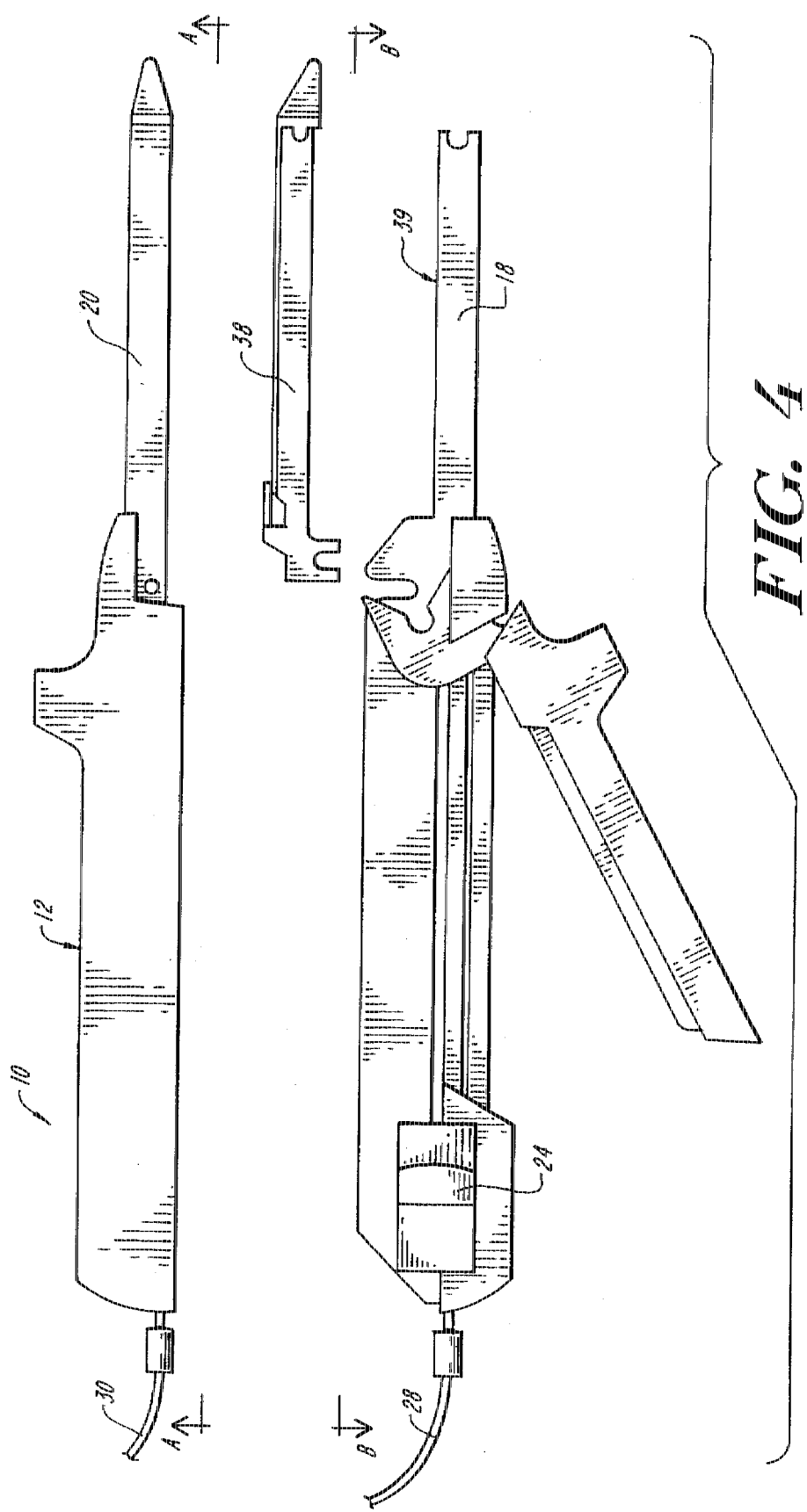
FIG. 4 is an exploded side view of the electrosurgical cutting tool illustrated in FIG. 3.
Figure 6:
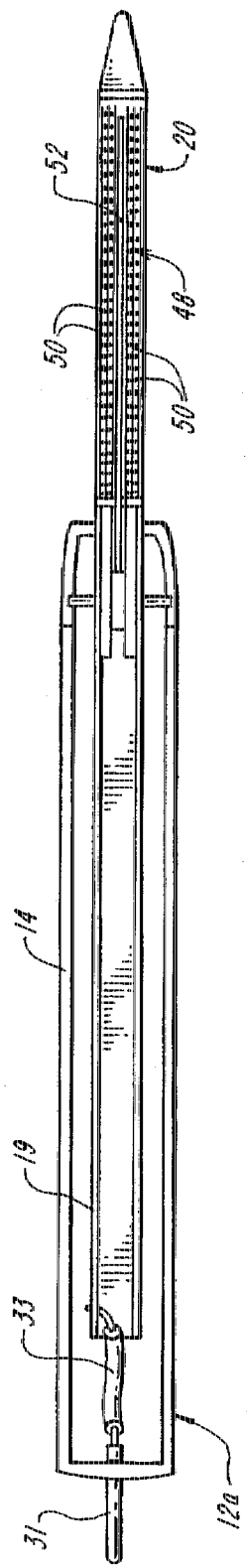
FIG. 6 is a sectional view of the electrosurgical tool of FIG. 4 at lines B—B.
Figure 5:
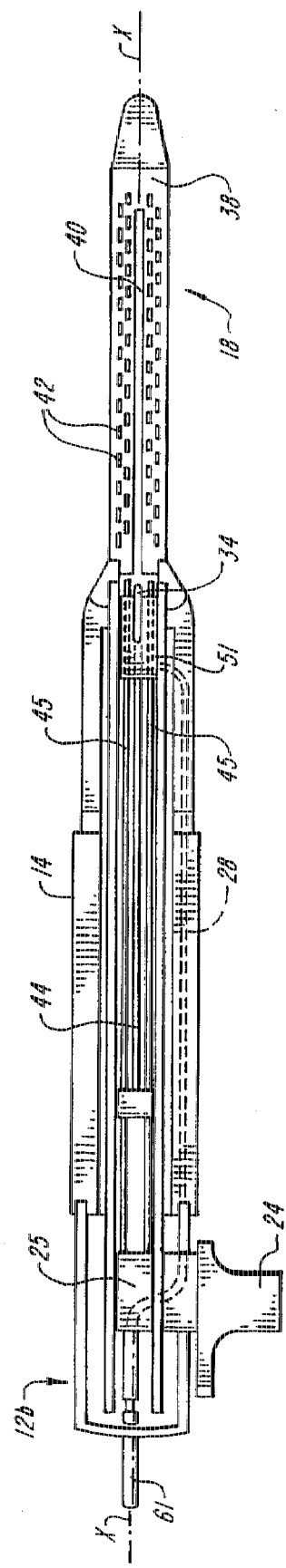
FIG. 5 is a sectional view of the electrosurgical tools of FIG. 4 at lines A—A.
Figure 7:
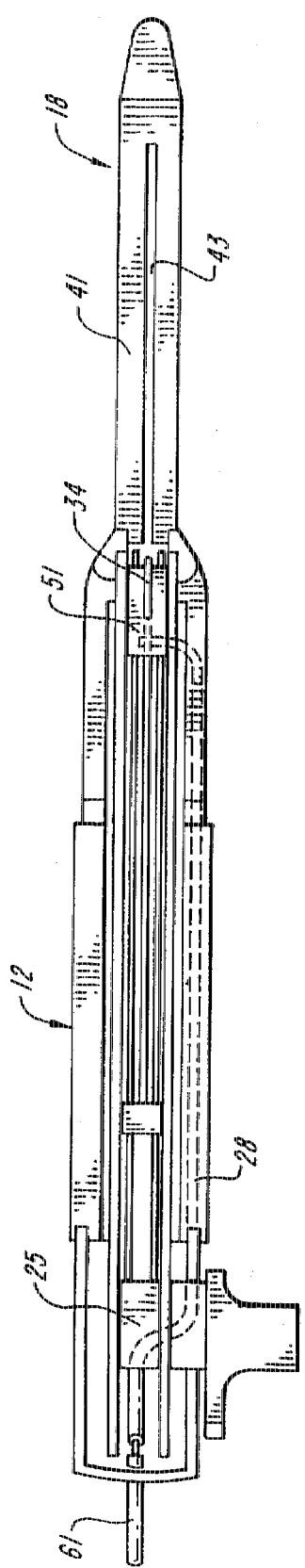
FIG. 7 is a sectional view of the electrosurgical tool of FIG. 4 at lines B—B in an embodiment which does not include a surgical staple cartridge.

FIG. 3 further illustrates an electrosurgical generator 26 which serves as an energy source from which electrical current, preferably in the radio frequency range, is communicated to the cutting tool through insulated wire 28 and connector 63. Insulated wire 30 communicates through connector 31 and return wire 33 to a conductive portion of tyne 20 which serves as the ground or return electrode. A power switch 32, preferably in the form of a foot petal, may be used to break or close the generator 26 circuitry and thus inhibit or transmit the power supplied to the cutting tool. Alternatively, a power switch may be disposed on a portion of the cutting tool such as the housing 12.

The circuit representing the power generator 26, the active electrode (e.g., blade 34), the return wire electrode, and the control module 26a, and impedance monitor 26b is electrically isolated to control the application of surgical energy by the tool. The control module 26a can regulate the electrosurgical energy delivered to the cutting blade 34, according to the measured tissue impedance determined by the impedance monitor 26b. As noted, the impedance monitor generates a signal representative of tissue impedance by quantifying the current received at the return electrode, which is a conductive portion of the tyne 20. The tissue impedance signal is communicated to the control module which in mm adjusts the applied electrosurgical energy to maintain a measured tissue impedance within a preselected range. Accordingly, electrosurgical power adjustments are made automatically to maintain a skin or tissue impedance to within a safe and operable range, independent of the speed and operator technique in using the tool 10.

In particular, for radio frequency energy, the range of measured tissue impedance is between 20 and 500 Ohms. When operating in this range, tissue incisions occur with effective cell heating, and further the tissue is cauterized, without burning, to prevent or minimize bleeding.

Although the control module 26a and impedance monitor 26b are shown connected to the power generator 26, it should be apparent that their specific location is irrelevant as long as they permit the simultaneous control and measurement of tissue impedance during the operation of the tool 10. They can thus be easily located on the tool 10.

Blade 34 of tool 10 preferably is able to be retracted when not in use, and moved forward along a cutting path to effect cutting of tissue.

The energy requirements of the electrosurgical tool of the present invention are dynamic and depend to a great extent upon the impedance values of the tissue encountered by the active electrode, e.g., blade 34, during cutting procedures. The impedance of tissue varies among tissue types and the amount of blood present in or around the tissue. The amount of current delivered by the tool to the tissue is a function of the impedance of the tissue. Where tissue contacted has a lower impedance value, less electrosurgical energy will be delivered to the blade 34 by operation of the impedance monitor 26b and control module 26a, and, conversely, more electrosurgical energy will be delivered to the blade 34 when the tissue has a higher impedance value. Generally, the mount of current delivered to tissue ranges between about 0.5 and 2.0 amps. The voltage applied to the tissue between the blade and the return electrode typically is between about 50 to 100 volts rms. These values are typical and are varied automatically to maintain a nearly constant current in the tissue during operation of the tool 10.

Surgical tool 10 is particularly well adapted for use in surgical procedures which require transection of an organ such as the intestine. In operation, the tissue (e.g., intestine) is placed within space 22 defined by tynes 18 and 20. The blade is moved forward along the longitudinal axis x of tynes 18 and 20 by movement of lever 24. As the blade moves forward, it passes through the tissue causing it to be severed. Simultaneously, electrical energy (e.g., radio frequency energy), which may be activated for example by foot switch 32, is delivered to the tool. The electrosurgical current is communicated from the blade 34 to the tissue adjacent the blade and in the vicinity of the incision. Current should be delivered through the blade to the tissue during the entire cutting procedure.

The application of electrical energy in this manner provides two advantages. Electrosurgical energy is delivered through the blade to adjacent tissue to allow for more effective cutting action, and to promote cauterization and/or tissue fusion which effectively eliminates all or substantially all bleeding which results from the incision. The cauterization and/or fusion effect imparted to tissue minimizes blood loss and increases the safety of the surgical procedure as cauterization occurs at substantially the same time that the incision is made. Furthermore, the speed at which the incision is made is generally irrelevant since the control module 26a will vary the applied energy to maintain a nearly constant tissue impedance.

In a preferred embodiment of the invention, the electrosurgical tool 10 also includes a staple cartridge 38 which houses a supply of surgical staples to be supplied adjacent the incision. The staples may be deployed in one or more linear rows on either side of the incision to assist in closing the incision and sealing the severed end of the organ. The staples are deployed nearly simultaneously with the cutting action of the blade and the tissue fusion effect imparted by the electrical energy.

One skilled in the art will appreciate that a variety of materials are well suited for the manufacture of the electrosurgical tool 10 shown in FIGS. 2–6. For example, housing 12 and cartridge 38 may be made from or coated with various non-conducting polymers. The conductive components of the tool may be made of various metals, including surgical grade stainless steel and aluminum.

Tool 10 is further described in copending U.S. patent application Ser. Nos. 786,572, filed Nov. 1, 1991, and hereby incorporated by reference.

Figure 8:
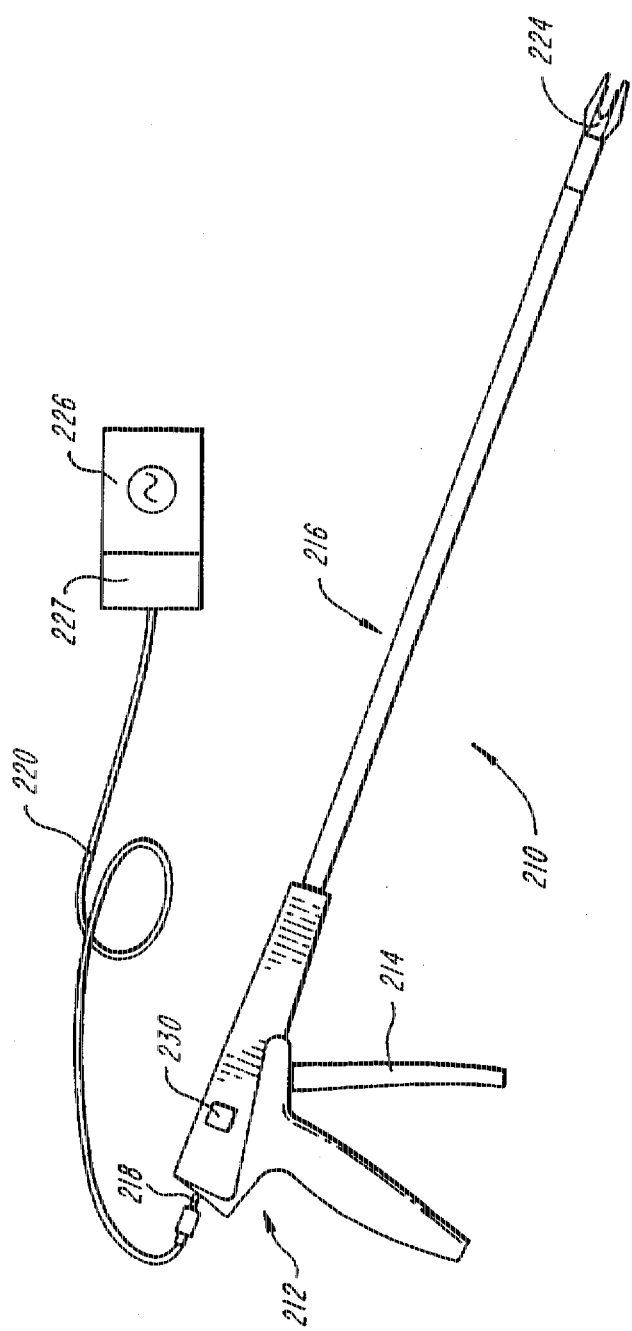
FIG. 8 is a schematic view of an electrosurgical clip application device employed in an impedance feedback electrosurgical system according to the invention.
Figure 9:
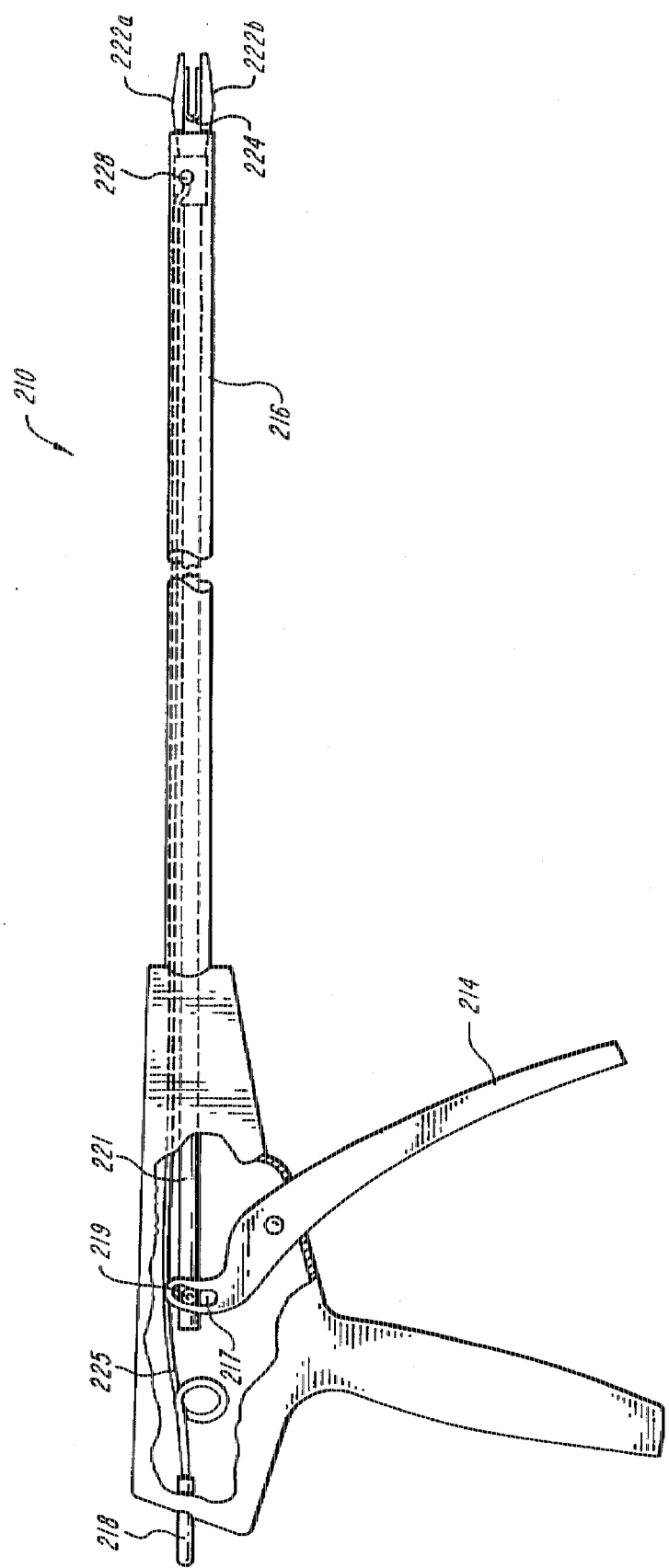
FIG. 9 is a side, partially cut-a-way view of the electrosurgical clip applicating device of FIG. 8.
Figure 10:
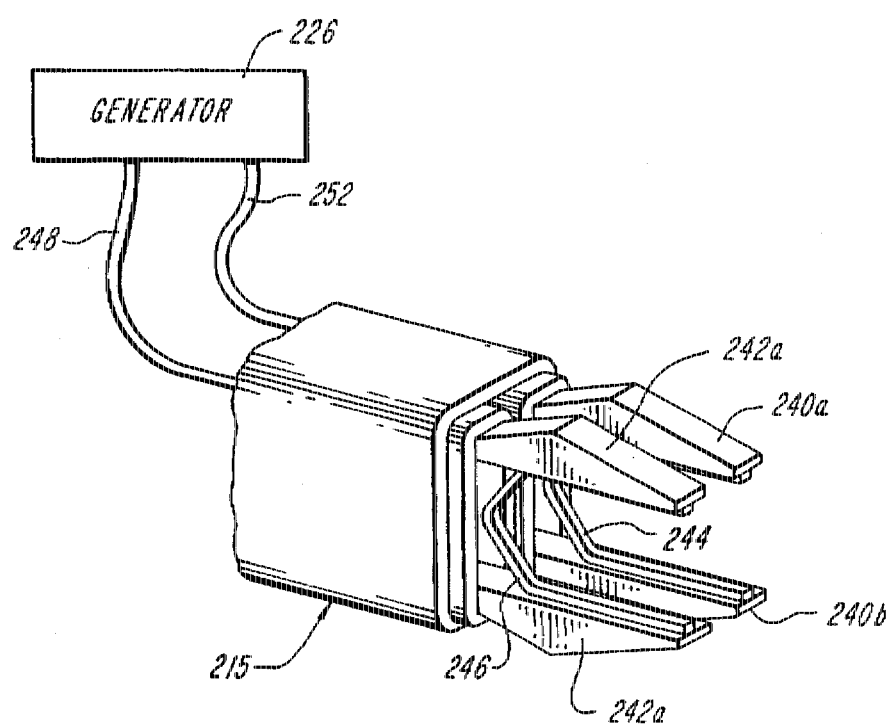
FIG. 10 is a schematic view showing a forward, clip deploying portion of a bipolar electrosurgical clip applicating device employed in an impedance feedback electrosurgical system according to the invention.

FIGS. 8 through 10 illustrate other electrosurgical tools that may be used with the impedance feedback system of the invention. FIGS. 8 and 9 illustrate an electrosurgical clip applicating device 210 comprising a handle portion 212 having a trigger mechanism 214. Adjacent the handle is an elongate member 216 which houses a supply of surgical clips (not shown) as well as an actuating mechanism, described below, which assists in deploying the clips. The handle 212 also includes an electrical connector port 218 which is connected to duplex insulated wire 220, comprising an internal active wire and an internal return wire which, respectively, communicate electrosurgical energy to and from generator 226.

An actuating mechanism adaptable for use with tool 210 is illustrated in FIG. 8. The actuating mechanism preferably includes an actuating rod 221 which communicates with the trigger mechanism 214 through a catch 219 which mounts within groove 217 of trigger 214. Actuating rod 221 also communicates with paired clamping jaws 222a, 222b which extend from a distal end of barrel 216. The clamping jaws 222a, 222b are adapted to engage and deploy a surgical clip 224. Surgical clips can be deployed by activation of the trigger mechanism 214, causing actuating rod 221 to move backwards (toward the handle 212) while closing clamping jaws 222a, 222b together. When the clamping jaws 222a, 222b are closed, the surgical clip 224 disposed between the jaws is clamped about a duct or vessel. Once a clip is deployed, a new clip may be positioned between clamping jaws 222a, 222b either automatically or manually.

An impedance and power control subsystem 227 functions like the combination of impedance monitor 116 and power control module 118 described in FIG. 1. Accordingly, subsystem 227 measures the tissue impedance and regulates the power applied to the tool 216 via the active wire of duplex wire 220.

Although the subsystem 227 is illustrated to be located with the generator 226, it is understood that its components and functions can easily be implemented at other locations, most readily within the tool 210.

Electrosurgical generator 226, shown in FIG. 8, communicates with clipping device 210 through conductive duplex wiring 220 which connects to the clipping device through duplex port 218. As shown in FIG. 9, duplex port 218 communicates with internally conductive duplex wiring 225 which extends into the clipping device 210. One of the two conductive wires within duplex wire 225 is an active wire connected to the active wire of duplex wire 220 and is attached to a conductive portion of the activating mechanism which is in electrical communication with surgical clip 224 to be deployed, thereby functioning as the active electrode. The embodiment illustrated in FIG. 9 is configured such that the active wire 225 terminates in a connection point 228, which is in electrical communication with the surgical chip 224, and electrically isolated from the clamping jaws 222a, 222b. The other wire within the duplex wire 225 is a return wire and is attached to a conductive portion of the clamping jaws 222a and 222b. The conductive portion is electrically isolated from the active electrode, i.e., the surgical clip 224, and functions as the return electrode to the negative pole of the power generator 226. With this arrangement, the duplex wires 225 and 220 form an isolated circuit with the generator 226, the impedance and power control subsystem 227, the return electrode on the clamping jaws 222a and 222b, the active electrode 224, and the tissue when the tool 210 is in operation.

In an alternative embodiment (not illustrated), the active wire of duplex wire 225 may attach to actuating rod 221 which is made from a conductive material and which is in electrical communication with clamping jaws 222a, 222b. The portions of the clipping device 210 which are in electrical communication with the active wire of duplex wire 225 (e.g., actuating rod 221 and/or clamping jaws 222a, 222b) preferably are electrically isolated from the remainder of the tool. The return wire of duplex wire 225 in this configuration is then connected to a separate return electrode (not shown) arranged on the tool 210 such that it contacts the tissue during operation of the tool 210 and functions as the return electrode to the negative pole of the generator 226. Upon activating the delivery of current to tool 210, for example by activating switch 230, current will be delivered through the duplex wire 225 and communicated to the active electrode, i.e., the surgical clip 224, through actuating rod 221 and/or clamping jaws 222a, 222b. The return electrode receives the electrosurgical energy transmitted through the tissue from the active electrode.

FIG. 10 illustrates an alternative clip applying tool which can be used with the present invention. Reference numeral 215 represents a forward portion of the barrel 216 which is adapted to receive dual pairs of clamping jaws 240a, 240b and 242a, 242b. The clamping jaws 240a, 240b and 242a, 242b each communicate with their respective actuating mechanisms (not shown) which are electrically isolated from each other. Surgical clips 244 and 246 are shown positioned within jaws 240a, 240b and 242a, 242b.

An insulated wire 248 functions like the active wire of duplex wire 220 shown in FIG. 8 and communicates electrosurgical energy from generator 226 to clamping jaws 242a, 242b (or, alternatively, to the actuating mechanism associated with clamping jaws 242a, 242b). Wire 252 serves as a return wire which communicates between jaws 240a, 240b (or the actuating mechanism associated with jaws 240a, 240b). Upon activation of a trigger mechanism, jaws 240a, 240b and 242a, 242b close together to deploy clips 244 and 246. At the same time a control switch is activated to deliver electrical current to the actuating mechanism associated with jaws 242a, 242b and/or directly to jaws 242a, 242b, and hence to clip 246, which functions as the active electrode. When the clip 246 contacts tissue, current is conveyed to the tissue causing the tissue and clip to be fused together. The electrosurgical energy also promotes tissue-to-tissue fusion. The applied current is returned to generator 226 through clamping jaws 240a, and 240b, and wire 252.

Generator 226 supplies electrosurgical energy to the clipping device 210 in the manner described above. Virtually any generator able to provide electrosurgical energy for medical applications may be used with the present invention. Preferably, the generator is a voltage determinative, low source impedance generator which provides radio frequency energy. Preferably, a suitable generator can supply up to 2 amps of current and has an impedance value of less than 10 ohms. Further details regarding the energy requirements of tool 210 are discussed above with respect to cutting tool 10.

Figure 11A:
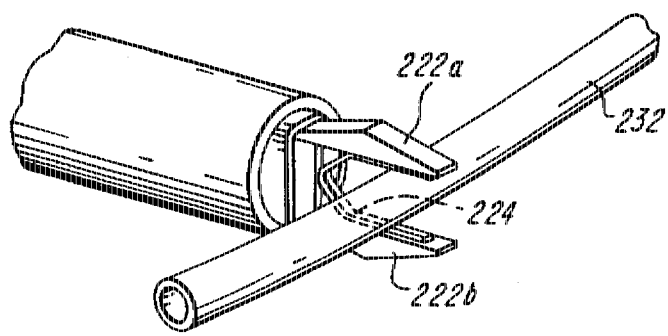
FIGS. 11A through 11C schematically illustrate the sequence in which a surgical clip is applied using the tool of FIG. 8.
Figure 11B:
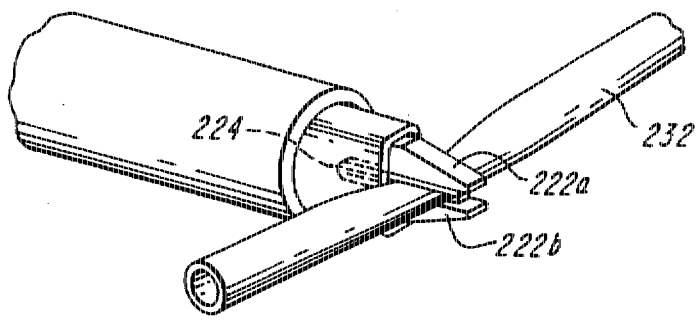
Figure 11C:
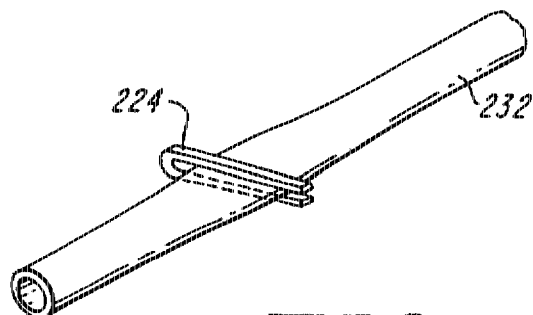

FIGS. 11A, 11B and 11C illustrate the manner in which surgical clips of FIGS. 8-10 are deployed. A vessel 232 to be ligated is disposed between clamping jaws 222a, 222b and surgical clip 224. Upon activating the triggering mechanism, the clamping jaws move together as shown in FIG. 11B, causing surgical clip 224 to close upon vessel 232. When the triggering action is completed the clip 224 remains adhered to the vessel 232 as illustrated in FIG. 11C. While the clip is applied over the vessel, electrosurgical energy is delivered through the clip 224, which functions as the active electrode. Current is maintained for a suitable period of time, usually 5 to 15 seconds, to enable tissue-to-clip and tissue-to-tissue fusion to occur. A return electrode isolated from and disposed on the clamping jaws 222a and 222b (not shown) communicates with the generator through a return wire to complete the circuit with the vessel 232.

The activating mechanism of clip activator 210 preferably is made of a conductive material which has a relatively high tensile strength. Exemplary materials include surgical grade stainless steel and aluminum. Clamping jaws 222a, 222b likewise are made of a surgically compatible, conductive material suitable to enable current to be communicated through the clamping jaws 222a, 222b to clip 224. The surgical clips 224 used with the clipping device of the invention may be with a variety of constructions and may be made of variety of conductive, surgically compatible materials which are well known in the art. As illustrated the surgical clip may be substantially U- or V-shaped, but various other shapes or constructions are possible as well.

The handle portion 212, trigger 214, and the barrel 216 are electrically isolated from the remainder of the device. Preferably, these components are made of, or are coated with, non-conductive materials such as suitable polymers.

The construction and operation of tool 210 is further described in copending parent application Ser. No. 07/786, 574, filed Nov. 1, 1992, now U.S. Pat. No. 5,207,691, which is incorporated herein by reference.

It is to be understood that the scope of the present invention encompasses electrosurgical tools having constructions other than those specifically described herein. The present invention is potentially applicable to any electrosurgical device utilized in an impedance feedback electrosurgical system according to the invention in which electrosurgical energy is delivered through the device to tissue in contact with the device.

What is claimed is:

1. An impedance feedback electrosurgical system for cutting and/or cauterizing living tissue comprising a bipolar electrosurgical device having a cutting portion including opposed, first and second tissue engaging surfaces defining a tissue engaging space therebetween, wherein one of the first or second surfaces includes an active, energy delivering electrode, and the other of the first or second surfaces includes a return electrode electrically insulated from the active, energy delivering electrode and being adapted to receive electrosurgical energy delivered by the active electrode through living tissue disposed within the tissue engaging space;

power means, in electrical communication with the active and return electrodes, for supplying radio frequency energy to the electrosurgical device;

impedance measurement means in electrical communication with the electrosurgical device and the power means, the impedance measuring means having a first electrical connection that is coupled to the return electrode for measuring the electrical impedance of the living tissue disposed within the tissue engaging space based on current and voltage applied to the tissue, the impedance measurement means generating a tissue impedance signal representative of tissue impedance; and power control means, in circuit with the electrosurgical device, the impedance measurement means and the power means, for regulating the electrosurgical energy delivered to the living tissue disposed within the tissue-engaging space by the active, energy delivering electrode in response to the impedance signal to maintain the tissue impedance within a preselected range.

2. The electrosurgical system of claim 1 wherein the range of impedance values is between about 20 Ohms and about 500 Ohms.

3. The electrosurgical system of claim 1 wherein the power control means regulates the energy applied to the active electrode by varying the voltage applied thereto.

4. The electrosurgical system of claim 1 further comprising activation means for selectively activating the power means to deliver electrosurgical energy to the active, energy delivering electrode.

5. The electrosurgical system of claim 1 wherein the electrosurgical device is an electrosurgical cutting device adapted to cut and substantially simultaneously cauterize the tissue disposed in the tissue engaging space located between the active and return electrodes.

6. The electrosurgical system of claim 1 further including a cutting element associated with one of the first or second members, the cutting element being movable between a non-operative position within one of the first or second members and an operative position.

7. The electrosurgical system of claim 6 wherein the cutting element is the energy delivering electrode.

8. The electrosurgical system of claim 1 wherein the voltage delivered to the electrosurgical device by the power means is between about 50 volts and about 100 volts RMS.

9. The electrosurgical system of claim 1 further comprising acoustical warning means, responsive to the tissue impedance signal generated by the impedance measurement means, for informing the user of a change in a measured tissue impedance.

10. The electrosurgical system of claim 1 further comprising acoustical warning means, responsive to the tissue impedance signal generated by the impedance measurement means, for alerting a user that the measured tissue impedance is outside of the preselected range.

11. An impedance feedback electrosurgical system comprising an electrosurgical device having a cutting portion including opposed, first and second tissue engaging elements defining a tissue engaging space therebetween;

an active, energy delivering electrode for cutting and cauterizing living tissue, housed on one of the first or second tissue engaging elements, the active electrode being movable between an inoperative position within one of the first or second tissue engaging elements and an operative, tissue affecting position;

a return electrode housed on the other of the first or second tissue engaging elements, the return electrode being electrically insulated from the active electrode and being adapted to receive electrosurgical energy delivered by the active electrode through the tissue;

power means for supplying radio frequency energy to the electrosurgical device, the power means being in electrical communication with the active and return electrodes;

impedance measurement means in electrical communication with the electrosurgical device and the power means, the impedance measuring means having a first electrical connection that is coupled to the return electrode for measuring the electrical impedance of the tissue disposed within the tissue engaging space based on current and voltage applied to the tissue, the impedance measurement means generating a tissue impedance signal representative of tissue impedance; and power control means, in circuit with the electrosurgical device, the impedance measurement means and the power means, for regulating the electrosurgical energy delivered to the tissue disposed within the tissue-engaging space by the active, energy delivering electrode in response to the impedance signal to maintain the tissue impedance within a preselected range.

* * * * *

UNITED STATES PATENT AND TRADEMARK OFFICE
CERTIFICATE OF CORRECTION

PATENT NO. : 5,713,896
DATED : February 3, 1998
INVENTOR(S) : Paul C. Nardella

It is certified that error appears in the above-identified patent and that said Letters Patent is hereby corrected as shown below:

| Column | Line(s) | Reads | Should Read |
| --- | --- | --- | --- |
| Cover | Inventor | North Easton, Mass. | Wareham, Mass. |
| 2 | 8 | mount | amount |
| 4 | 13 | circuit, | circuit |
| 6 | 22 | mm | turn |
| 6 | 57 | mount | amount |
| 9 | 61 | Which | which |

Signed and Sealed this

First Day of June, 1999

Attest:

Q. TODD DICKINSON

*Attesting Officer*     Acting Commissioner of Patents and Trademarks